United States Patent [19]

Morell

[11] Patent Number: 5,389,070
[45] Date of Patent: Feb. 14, 1995

[54] SYRINGE APPARATUS WITH A FLUID RESEVOIR FOR INJECTION AND ASPIRATION OF FLUIDS

[75] Inventor: Robert C. Morell, Winston-Salem, N.C.

[73] Assignee: Wake Forest University, Winston-Salem, N.C.

[21] Appl. No.: 33,633

[22] Filed: Mar. 16, 1993

[51] Int. Cl.⁶ ............... A61M 31/00; A61M 5/178
[52] U.S. Cl. ................................ 604/51; 604/183
[58] Field of Search ............. 604/181, 183, 191, 246, 604/248, 227, 51–53

[56] References Cited

U.S. PATENT DOCUMENTS

| | | | |
|---|---|---|---|
| 1,832,533 | 11/1931 | Creasy | 604/227 |
| 2,972,991 | 2/1961 | Burke . | |
| 3,203,455 | 8/1965 | Horabin | 604/183 X |
| 4,044,758 | 8/1977 | Patel | 604/191 X |
| 4,471,765 | 9/1984 | Strauss et al. | 604/191 X |
| 4,563,175 | 1/1986 | LaFond | 604/155 |
| 4,838,855 | 6/1989 | Lynn | 604/49 |
| 4,838,857 | 6/1989 | Strowe et al. | 604/67 |
| 4,904,243 | 2/1990 | Bruera | 604/183 |

OTHER PUBLICATIONS

Morell, R. C., A. S. Foreman, H. I. Kashtan and R. Brooker, "A Convenient Adaptation of the Control Syringe," *Regional Anesthesia*, vol. 17, No. 2, Mar.–Apr. 1992.

*Primary Examiner*—John D. Yasko
*Assistant Examiner*—Adam J. Cermak
*Attorney, Agent, or Firm*—Dann, Dorfman, Herrell, and Skillman

[57] ABSTRACT

A syringe apparatus is provided having a first control syringe with a hypodermic needle for injecting medication into a patient. A three-way stopcock interconnects the first syringe with the hypodermic needle and also interconnects the first syringe with a second reservoir syringe. A handle lever on the stopcock may be positioned to provide a first fluid flow path between the first syringe and the hypodermic needle to permit injection of medication into the patient. The handle lever of the stopcock may alternatively be positioned to provide a second fluid flow path to permit the first syringe to be refilled with medication from the second reservoir syringe for subsequent injection into the patient. The refilling of the first syringe from the reservoir syringe may be effected without removal of the needle from the patient and without disassembly of the first syringe.

22 Claims, 1 Drawing Sheet

SYRINGE APPARATUS WITH A FLUID RESEVOIR FOR INJECTION AND ASPIRATION OF FLUIDS

FIELD OF THE INVENTION

The present invention generally relates to a method and apparatus for transmitting a fluid to or from a patient and, more specifically, to a syringe apparatus and method for precisely administering selected amounts of medication, such as an anesthetic, to a patient using a control syringe for the administration of the medication and a reservoir syringe for refilling the control syringe for administration of additional medication.

BACKGROUND OF THE INVENTION

The use of hypodermic syringes for administering medications to patients has been known for a relatively long period of time. Over the years, however, physicians have attempted to modify and refine the basic design of the syringe in effort to improve the technique of administering medications to patients.

One of the problems frequently encountered in using a conventional hypodermic syringe is that it often becomes desirable, as well as sometimes necessary, for the physician to operate the syringe with one hand so that the physician's other hand remains free to perform other tasks. A three-ring, or finger-control, syringe has been developed to facilitate one-handed operation. The conventional three-ring syringe allows the physician to retract and engage the plunger of the syringe to permit one-handed filling, aspirating, and injecting. The three-ring syringe has been useful in facilitating accurate positioning of the hypodermic needle in the patient as well as permitting the administration of precise amounts of medication.

Despite the development of the three-ring syringe, a practical problem still remains. Whenever the medication to be administered to a patient exceeds the capacity of the conventional three-ring syringe, the syringe must be refilled during use in order to administer the proper amount of medication to the patient. For example, a conventional three-ring control syringe for injecting a regional anesthetic may have a capacity of approximately 10 cc's. However, many regional anesthetics, such as axillary blocks, interscalene blocks, and femoral-sciatic nerve blocks, require an injection of 30 to 60 cc—s of anesthetic. Since it is not always convenient or practical to use a syringe having a sufficiently large capacity, the conventional practice is either to disassemble the needle from the syringe or to withdraw the needle entirely from the patient to permit refilling of the control syringe. Unfortunately, the conventional practice of disassembling the needle from the syringe results in an increased risk of contamination as well as the added inconvenience and danger of trying to reassemble the refilled syringe to the needle while the needle remains in the patient. Similarly, the conventional practice of withdrawing the needle from the patient to permit refilling of the syringe also increases the risk of contamination as well as the possibility of an accidental needle stick during needle removal or reinsertion.

In accordance with the present invention, a closed system of administering medication is provided that obviates the need either to disconnect the needle from the control syringe or to remove the needle from the patient in order to refill the syringe to administer medication in volumes greater than the capacity of the control syringe. The present invention provides a syringe apparatus and method for administering medications to patients with improved safety to both the physician and the patient.

SUMMARY OF THE INVENTION

In accordance with the present invention, a syringe apparatus and method are provided for administering a fluid, such as a medication or anesthetic, to a patient. The syringe apparatus includes a first control syringe having a generally hollow tube and a plunger for longitudinal displacement within the hollow tube. The hollow tube includes a tip at one end of the tube that provides a fluid conduit port for transmitting a fluid to or from the hollow tube upon displacement of the plunger within the hollow tube. A mouth-like opening is provided at the other end of the hollow tube to receive the plunger. The plunger includes a piston for positioning in sealing engagement with the inside wall of the hollow tube and an actuator handle for effecting longitudinal displacement of the piston within the hollow tube to provide fluid transmission to or from the hollow tube through the fluid conduit port at the tip of the first end of the hollow tube.

A reservoir container is provided for holding a predetermined supply of the fluid, such as a selected medication, to be administered to the patient. The reservoir container may be in the form of a second reservoir syringe for containing a supply of the medication to be administered to the patient.

A three-port valve, in the form of a three-way stopcock, is provided for connection to the tip of the first syringe to control fluid flow from the first syringe. The valve includes a first outside port for transmitting fluid, a second reservoir port for connection with the reservoir container, and a third syringe port for connection with the first syringe. The syringe apparatus includes fluid directing means, such as a hypodermic needle, connected with the outside port of the valve for precisely transmitting fluid. The reservoir port of the valve is connected with the reservoir container to provide fluid communication between the reservoir container and the valve. The syringe port of the valve is connected with the tip of the hollow tube of the first syringe to provide fluid communication between the valve and the hollow tube of the first syringe. In order to control fluid flow relative to the first syringe, the valve alternatively provides a first fluid flow path internal to the valve between the reservoir port and the syringe port and a second fluid flow path internal to the valve between the syringe port and the outside port. A selector in the form of a handle lever is provided on the valve for alternatively selecting the first and second fluid flow paths through the valve.

In operation, a closed system is provided whereby fluid within the first syringe may be administered to the patient when the selector is set to provide the second fluid flow path through the valve. Alternatively, when the selector is set to provide the first fluid flow path through the valve, the first syringe may be refilled from the reservoir container without removing or withdrawing the hypodermic needle from the patient and without disconnecting or disassembling the first syringe. After the first syringe has been refilled, the medication may be administered to the patient by using the selector to again provide the second fluid flow path through the valve.

The system may also be used in reverse to drain fluid from a patient. The fluid from the patient may be withdrawn into the syringe along the second fluid flow path. The fluid may then be transferred from the syringe along the first fluid flow path into the reservoir container.

BRIEF DESCRIPTION OF THE DRAWINGS

The foregoing summary as well as the following detailed description of the preferred embodiments of the present invention will be better understood when read in conjunction with the appended drawings, in which.

DETAILED DESCRIPTION OF THE PREFERRED EMBODIMENTS

Figure 1:
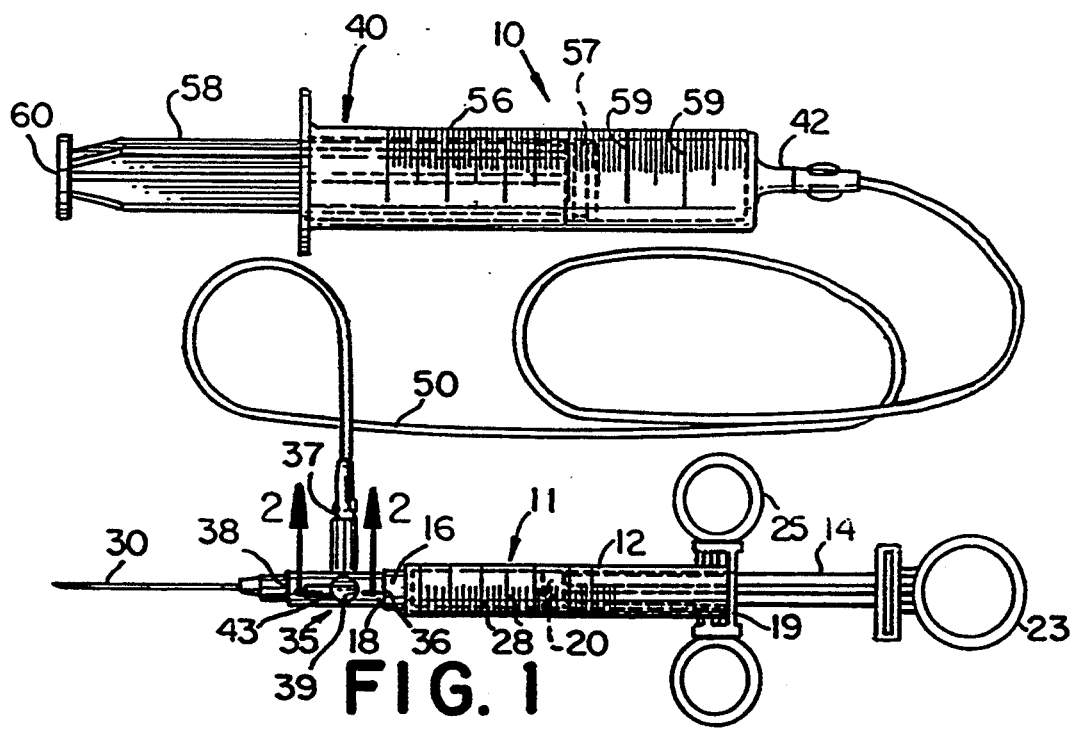
FIG. 1 is a schematic plan view of a syringe apparatus in accordance with the present invention.

Referring to FIG. 1, a syringe apparatus, generally designated 10, is provided for administering medication, such as a local anesthetic, to a patient. The syringe apparatus 10 may be useful for animals as well as human beings.

The syringe apparatus 10 includes a first syringe 11 that is connected by an elongated, flexible, plastic tube 50 to a reservoir container in the form of a second reservoir syringe 40. A three-port valve 35 in the form of a three-way stopcock interconnects the first syringe 11 with a hypodermic needle 30 for the first syringe and interconnects the first syringe 11 with the tube 50 connected to the reservoir syringe 40.

The first syringe 11 is in the form of a three-ring or finger-control syringe that enables the physician or other practitioner to administer medication such as a local anesthetic in a precise amount at a precise location. The first syringe 11 includes a generally hollow tube 12 and a plunger 14 that slides longitudinally within the hollow tube 12.

A nozzle tip 16 is provided at one end of the generally hollow tube 12 of the first syringe. The nozzle tip 16 includes a fluid port 18 in the form of a central fluid conduit that communicates with the interior of the hollow tube 12 to permit transmission of fluid to and from the hollow tube. The other end of the generally hollow tube 12 includes a mouth-like opening 19 for receiving the plunger 14. A flexible sealing piston 20 is supported on the end of the plunger 14 that is inserted into the generally hollow tube 12 through the mouth opening 19. The piston 20 sealably engages the inside walls of the hollow tube 12. As the plunger 14 is moved in and out of the hollow tube, an air-tight seal remains formed between the piston 20 and the inner wall of the hollow tube 12. The other end of the plunger 14 projects outwardly from the mouth opening 19 of the hollow tube 12 to provide an actuator 23 for effecting longitudinal displacement of the piston 20 within the hollow tube. Displacement of the piston 20 within the hollow tube 12 causes fluid transmission through the fluid port 18 at the nozzle tip 16 of the syringe 11.

For convenience of operation, the actuator 23 for the plunger 14 may include a finger loop attached to the exposed end of the plunger 14. A pair of finger loops 25 may be removably or permanently mounted about the mouth opening 19 of the hollow tube 12 for cooperating with the finger loop on actuator 23 of the plunger 14 to facilitate one-handed operation of the first syringe 11. Index lines 28 are provided on the exterior of the hollow tube 12 of the first syringe to permit the amount and flow rate of medication to be accurately metered during injection or aspiration. The index lines 28 permit precise metering of fluid to or from the hollow tube 12 of the first syringe 11.

The first syringe 11 also includes fluid directing means in the form of the hypodermic needle 30 for precisely transmitting fluid to and from the hollow tube 12 of the first syringe 11 through the fluid port 18 at the nozzle tip 16.

The second syringe 40 serves as a reservoir container for holding fluid. The reservoir container may also be in the form of a bottle or bag or any other convenient fluid storage container. The second syringe 40 includes a generally hollow tube 56 and a plunger 58 having a flexible sealing piston 57 in sealing engagement with the inside wall of the hollow tube 56. The plunger 58 includes an actuator handle 60 to effect longitudinal displacement of the piston 57 within the hollow tube 56. As the plunger is moved, displacement of the piston 57 causes a fluid flow through the tip 42 of the hollow tube 56. Index lines 59 are provided on the outside of tube 56 to provide indication of the volume of fluid in the hollow tube 56. The index lines 59 also permit precise metering of fluid in or out of the second syringe 40.

The three-port valve, generally designated 35, interconnects the hypodermic needle 30 to the nozzle tip 16 of the generally hollow tube 12. The valve provides rigid support so that the hypodermic needle is held and supported in fixed position relative to the generally hollow tube 12 of the first syringe 11 to facilitate insertion of the needle into a patient. The three-port valve 35 also serves to interconnect the reservoir container in the form of the second syringe 40 to the first syringe 11. In order to ensure fluid-tight connections, LuerLok fittings may be provided for sealed connections at each of the ports of the three-port valve and at the nozzle tip 42 of the second syringe 40.

The valve 35 may be in the form of a three-way stopcock having a first port 38 that serves as an outside port for sealed connection to the hypodermic needle 30. The three-port valve 35 also includes a second port 37 that serves as a reservoir port for sealed connection with the second syringe 40. For this purpose, the plastic tube 50 is connected and sealed to the second port 37 of the three-port valve 35 at one end and at the other end is connected and sealed to the nozzle tip 42 of the second syringe 40 to effect fluid communication between the second syringe 40 and the second port 37 of the three-port valve. The three-port valve 35 also includes a third port that serves as a syringe port for sealed connection and attachment to the nozzle tip 16 of the first syringe 11 to effect fluid communication between the valve and the first syringe 11 through the fluid port 18 at the nozzle tip 16 of the first syringe 11.

Figure 2:
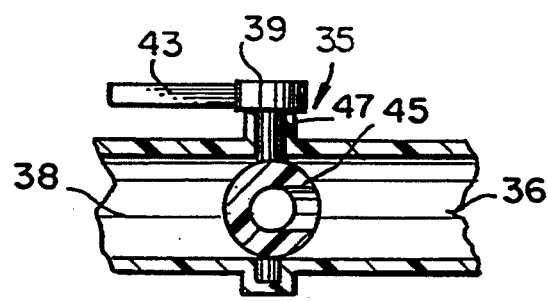
FIG. 2 is an enlarged schematic cross-sectional view of a three-port valve of the syringe apparatus taken along line 2—2 of FIG. 1, but with internal seals removed to better show fluid flow paths through the valve.

The valve 35 functions to alternatively provide first and second fluid flow paths through the valve. A selector 39 is provided on the valve 35 for alternatively selecting either the first or the second fluid flow path. The selector 39 preferably includes a handle lever 43 to facilitate one-handed operation of the valve. The flow of fluid through the valve is controlled by manual rotation of the selector 39 between a first position corresponding to the first fluid flow path and a second position corresponding to the second fluid flow path. The selector 39 may also be turned to an off position to shut off the valve completely. The direction of fluid flow through the valve is controlled by the position of an internal gate 45. As best shown in FIG. 2, the gate 45 is connected to the external selector 39 by valve stem 47. By rotating handle lever 43 to the first position shown in FIG. 3, the outside port 38 is blocked and the reservoir port 37 is connected in fluid communication with the syringe port 36 to permit fluid to pass between the second syringe 40 and the first syringe 11. By rotating the lever 43 to the second position shown in FIG. 4, the reservoir port 37 is then blocked and the syringe port 36 is connected in fluid communication with the outside port 38 to permit fluid flow between the hypodermic needle 30 and the first syringe 11.

Figure 3:
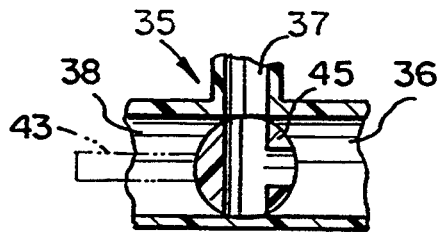
FIG. 3 is an enlarged schematic fragmentary sectional view of the three-port valve taken from the top of FIG. 1, but with internal seals removed to more clearly show a first fluid flow path within the valve and with a valve handle depicted in phantom to show relative positioning of the handle.

In greater detail, when handle lever 43 is rotated to align with the central axis of the hypodermic needle 30, as shown in FIG. 3, the outside port 38 to the hypodermic needle is sealed to fluid flow by gate 45. The first fluid flow path is thereby established through the valve 35 between the syringe port 36, which provides fluid communication with the generally hollow plastic tube 12 through the fluid port 18 at the nozzle tip 16 of the first syringe 11, and the reservoir port 37, which provides fluid communication with the second syringe 40 through the tube 50. In this first position of the handle lever 43, the valve 35 enables fluid flow between the second syringe 40 and the first syringe 11 with the direction of fluid flow being controlled by the direction of longitudinal displacement of the plunger 14 within the hollow tube 12. If the plunger 14 is withdrawn or retracted away from the generally hollow tube 12, fluid from the second syringe 40 will be sucked through tube 50, then through valve 35 and into the generally hollow tube 12. Alternatively, if the plunger is forced into the generally hollow tube 12, fluid in the first syringe will be forced through the valve 35, then through hollow tube 50 and into the second syringe 10.

Figure 4:
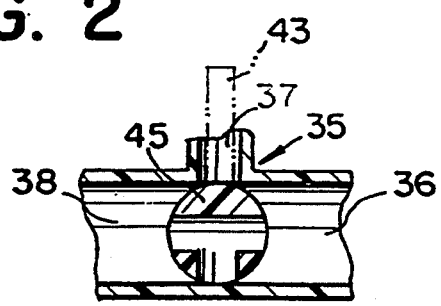
FIG. 4 is an enlarged schematic fragmentary sectional view of the three-port valve, but with internal seals removed to more clearly show a second fluid flow path within the valve and with the valve handle depicted in phantom to show relative positioning of the handle.

As shown in FIG. 4, when the handle lever 43 is turned to the second position generally aligned with reservoir port 37 and generally perpendicular to the central axis of the hollow tube 12 and the needle 30, the gate 45 seals the reservoir port 37. The second fluid flow path is thereby established between the syringe port 36, which provides fluid communication with the hollow tube 12 of the first syringe 11, and the outside port 38, which provides fluid communication to the hypodermic needle 30. When the handle lever 43 is positioned in this second position, the first syringe 11 may be operated to aspirate fluid through the hypodermic needle 30, then through valve 35 and into the generally hollow tube 12 of the first syringe 11. Aspiration is effected by moving the plunger 14 so as to displace the piston 20 in a longitudinal direction outwardly of the generally hollow tube 12. Alternatively, if the plunger is pushed into the generally hollow tube 12 so as to longitudinally displace the piston 20 inwardly of the hollow tube, fluid contained in the hollow tube 12 will be forced through the valve 35 and through the hypodermic needle 30.

In operation, the second reservoir syringe 40 is filled with a selected medication, for example, a selected anesthetic such as bupivacaine, lidocaine, or mepivacaine. The reservoir syringe 40 may be supplied by a manufacturer already prefilled with a selected medication or the reservoir syringe 40 may be filled as needed by the physician or other practitioner. If a prefilled reservoir syringe 40 is utilized, it may be desirable to manufacture the components of such syringe out of a suitable material, such as a glass hollow tube 56, to prevent or deter any adverse effects on the contained medication during long-term storage.

The reservoir syringe 40 may also be filled by the physician or other practitioner from a storage vial of medication by temporarily attaching a needle to the end of the reservoir syringe 40 to withdraw the medication from the vial. After the needle is attached to the reservoir syringe 40, the needle is inserted into the vial with the plunger 58 fully depressed into the generally hollow tube 56 of the reservoir syringe 40 in order to reduce the amount of air trapped within the hollow tube 56. The plunger 58 is then retracted until the desired amount of medication has filled the hollow tube 56 of the reservoir syringe 40 as determined by the index lines 59 on the hollow tube 56. The reservoir syringe 40 may also be filled without using a needle. For example, the reservoir syringe 40 may be filled by removing the plunger 58 to permit filling through the open end of the syringe 40. Alternatively, the reservoir syringe 40 may be filled by attaching a tube to the tip 42 of the syringe 40 for insertion into a storage container of medication so that medication can be sucked from the storage container and into the reservoir syringe 40 by actuation of plunger 58.

After the reservoir syringe 40 is filled with the selected medication, the plastic tube 50 is connected to the tip 42 of the reservoir syringe 40 and to the second port 37 of the stopcock 35. Prior to connecting the tube 50 to the stopcock 35, air in the tube 50 may be forced out of the tube 50 by partial actuation of the plunger 58 into the hollow tube 56 of the reservoir syringe 40.

Next, the plunger 14 of the control syringe 11 is fully inserted into the hollow tube 12 and the handle lever 43 of the stopcock 35 is turned to the first position as shown in FIG. 3 so that medication can be transferred from the reservoir syringe 40 to the control syringe 11. The control syringe 11 is then filled with medication from the reservoir syringe 40 by withdrawing the plunger 14 from the hollow tube 12. The plunger 14 may be retracted by pulling the finger loop 23 away from finger loops 25 until the desired amount of medication as measured by index lines 28 fills the hollow tube 12. In order to exhaust any trapped air that is sucked into the hollow tube 12 of the first control syringe 11 during filling, the handle lever 43 of the stopcock 35 is then turned to the second position as shown in FIG. 4 so as to block the second reservoir port 37 and to provide fluid communication between the third syringe port 36 and the first outside port 38. The control syringe 11 is then held in a generally vertical, needle-up position and the plunger 14 is partially pushed into the hollow tube 12 to force the trapped air out of the syringe 11 through the hypodermic needle 30. At this point, the apparatus is primed and ready for administering medication to the patient.

For purposes of administering medication, the hypodermic needle is then inserted into the patient at a predetermined location. If desired, the plunger 14 may be slightly retracted to provide aspiration to ascertain proper needle placement. If the needle is properly positioned, the plunger 14 is then depressed into the hollow tube 12 thereby injecting the medication into the patient. The rate of injection can be monitored by observing the fluid level in the hollow tube in relation to the index lines 28.

After all of the medication in the hollow tube 12 is injected, additional medication from the reservoir syringe 40 may be administered to the patient without any need to remove the needle 30 from the patient or without any need to disassemble the first syringe 11. Instead, the handle lever 43 of the stopcock 35 is turned from the second position as shown in FIG. 4 to the first position as shown in FIG. 3 to permit closed-system refilling of the control syringe 11 from the reservoir syringe 40. A stopcock 35 having a relatively low coefficient of friction at the handle mount is desirable to permit relatively easy turning of the handle lever 43 between positions in order to facilitate turning of the handle lever by the same hand that holds the syringe. After the handle lever 43 is turned to the first position as shown in FIG. 3, the practitioner may then proceed to again fill the control syringe 11 by retracting the plunger 14 of the control syringe to suck medication from the reservoir syringe 40, through the stopcock 35, and into the hollow tube 12 of the control syringe 11. After the control syringe is refilled with medication from the reservoir syringe, the stopcock handle lever 43 is again turned from its first position as shown in FIG. 3 back to its second position shown in FIG. 4 to permit the additional medication contained within the refilled syringe 11 to be injected into the patient. The procedure of injecting medication into the patient and refilling the hollow tube 12 of the first control syringe 11 with additional medication may be alternated until the predetermined amount of medication, as measured by index lines 59 on the reservoir syringe 40, has been administered to the patient.

By using a syringe having finger loops 23 and 25 and a stopcock 35 having a handle lever 43 that turns relatively easily, the refilling, aspirating, and injecting of medication into a patient can be effected relatively easily by the physician or other practitioner using only one hand. Even more importantly, the refilling, aspirating, and injecting is effected through a closed system. In this regard, the control syringe 11 can be refilled with medication for administration to a patient without any need for withdrawal of the hypodermic needle 30 from the patient or without any need for the disassembly of the hollow tube 12 of the control syringe from the needle 30 and/or the stop-cock 35 to permit refilling.

As a safety improvement, the system remains closed to the outside environment during the refilling of the syringe and the administration of the medication to the patient from the refilled syringe. Once the syringe apparatus 10 is filled with medication and assembled, there is no need to open the system in order to inject a patient with an amount of medication that exceeds the capacity of the control syringe 11. As such, the system is less susceptible to contamination. In addition, the possibility of an accidental needle stick is greatly reduced. These safety factors are especially important in light of the increasing concern about accidental transmission of HIV or hepatitis.

While the syringe apparatus 10 has been developed primarily for use in administering medication to a patient, the apparatus assembly 10 may also be used for aspirating fluid from a patient. In order to use the syringe apparatus 10 as an aspirator, the needle 30 is inserted into the patient and the stopcock handle lever 43 is set to the second position as shown in FIG. 4. Retraction of the plunger 14 from the hollow tube 12 aspirates fluid from the patient into the generally hollow tube 12 of the control syringe 11. After aspiration of the fluid is completed, the stopcock handle lever 43 is turned to its first position as shown in FIG. 3 so that the fluid may be forced from the control syringe 11 into the reservoir syringe 40 or other reservoir container by either pressing plunger 14 into the hollow tube 12 of the control syringe 11 or by retracting plunger 58 from the generally hollow tube 56 of the reservoir syringe 40. If desired, the aspiration procedure may be repeated.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the following claims below.

What is claimed is:

1. A syringe apparatus for transmitting a fluid comprising:
   (a) a first syringe having a generally hollow tube and a plunger for displacement within the hollow tube, the hollow tube having a fluid port for transmitting fluid relative to the hollow tube and the plunger having a piston in sealing engagement with the hollow tube and an actuator for effecting longitudinal displacement of the piston within the hollow tube to provide fluid transmission through the fluid port;
   (b) a second syringe for containing the fluid;
   (c) a flexible connecting tube with a first end and a second end, the first end being connected with the second syringe;
   (d) a valve having an outside port for transmitting fluid, a reservoir port connected with the second end of the connecting tube, and a syringe port connected with the fluid port of the hollow tube, the valve providing a first fluid flow path between the reservoir port and the syringe port and a second fluid flow path between the syringe port and the outside port and the valve having a selector for alternatively selecting the first and second fluid flow paths; and
   (e) a hypodermic needle connected with the outside port of the valve so that the valve rigidly holds the hypodermic needle in fixed position relative to the first syringe.

2. The apparatus as recited in claim 1 wherein at least one of the first and second syringes includes index means to enable metering of a predetermined amount of fluid.

3. The apparatus as recited in claim 1 wherein at least one of the first and second syringes has index means to enable metering of a predetermined amount of fluid.

4. The apparatus as recited in claim 1 wherein the actuator comprises a finger loop and the hollow tube includes two finger loops for one-handed operation of the first syringe.

5. A method for administering a fluid to a patient comprising:
(a) providing a valve having a first port, a second port, and a third port and a manual actuator handle movable between at least a first position providing a first fluid flow path through the valve and at least a second position providing a second fluid flow path through the valve;
(b) connecting a hypodermic needle to the first port;
(c) connecting a container holding the fluid to be administered to the second port;
(d) connecting a first syringe to the third port;
(e) moving the actuator handle to the first position to select the first fluid flow path through the valve between the second port and the third port;
(f) actuating the first syringe after moving the actuator handle to the first position so that the fluid from the container flows through the first fluid flow path and fills the first syringe to a selected level;
(g) moving the actuator handle to the second position to select the second fluid flow path through the valve between the first port and the third port;
(h) inserting the hypodermic needle into a patient; and
(i) actuating the first syringe after moving the actuator handle to the second position so that the fluid in the first syringe flows through the second fluid flow path and is thereby administered through the hypodermic needle to the patient.

6. The method recited in claim 5 comprising the further steps of:
(a) refilling the first syringe by selecting the first fluid flow path through the valve and actuating the first syringe so that fluid from the container flows through the first fluid flow path and refills the first syringe to a selected level; and
(b) administering the fluid in the refilled first syringe to the patient by selecting the second fluid flow path through the valve and actuating the first syringe so that the fluid in the first syringe flows through the second fluid flow path and is thereby administered to the patient through the hypodermic needle.

7. The method recited in claim 6 wherein steps (a) through (b) of claim 6 are performed while keeping the first syringe connected with the third port and while keeping the hypodermic needle connected with the first port and inserted into the patient.

8. The method as recited in claim 5 wherein the fluid in the container is a medication.

9. The method as recited in claim 8 wherein the fluid in the container is an anesthetic.

10. The method as recited in claim 5 wherein the step of connecting the container to the second port is performed by providing an elongated flexible connecting tube and coupling a first end of the connecting tube to the second port and by coupling a second end of the connecting tube to the container holding the fluid to be administered.

11. The method as recited in claim 5 comprising the step of metering the fluid from the container.

12. The method as recited in claim 11 wherein the metering step is effected by providing a second syringe as the container and filling the second syringe with a predetermined amount of fluid.

13. A method for aspirating a fluid from a patient comprising:
(a) providing a valve having a first port, a second port, and a third port and having first and second fluid flow paths through the valve;
(b) connecting a hypodermic needle to the first port;
(c) connecting a container for holding aspirated fluid to the second port;
(d) connecting a syringe to the third port;
(e) selecting the second fluid flow path through the valve between the first port and the third port;
(f) inserting the hypodermic needle into the patient;
(g) actuating the syringe so that fluid in the patient flows through the second fluid flow path and fills the syringe to a selected level;
(h) selecting the first fluid flow path through the valve between the second port and the third port; and
(i) actuating the syringe so that the fluid from the syringe flows through the first fluid flow path and fills the container to a selected level.

14. The method recited in claim 13 comprising the further steps of:
(a) refilling the syringe with fluid from the patient by selecting the second fluid flow path through the valve and actuating the syringe so that fluid from the patient flows through the second fluid flow path and refills the syringe to a selected level; and
(b) filling the container with the fluid in the refilled syringe by selecting the first fluid flow path through the valve and actuating the syringe so that the fluid in the refilled syringe flows through the first fluid flow path and fills the container to a selected level.

15. The method recited in claim 14 wherein steps (a) through (b) of claim 14 are performed while keeping the first syringe connected with the third port and while keeping the hypodermic needle connected with the first port and inserted into the patient.

16. A method for transmitting a fluid comprising:
(a) providing a first fluid flow path between a reservoir container and a syringe having a hollow tube and a plunger, the first fluid flow path allowing fluid to be transmitted between the reservoir container and the hollow tube;
(b) providing a second fluid flow path between the syringe and a fluid directing means for directing fluid flow, the second fluid flow path allowing fluid to be transmitted between the hollow tube and the fluid directing means;
(c) positioning the fluid directing means at a selected position;
(d) alternatively selecting the first and second fluid flow paths;
(e) retracting the plunger so that fluid flows into the hollow tube along a selected one of the first and second fluid flow paths; and
(f) engaging the plunger into the hollow tube so that fluid flows out of the hollow tube along the selected one of the first and second fluid flow paths.

17. The method as recited in claim 16 comprising the step of repeating steps (d) through (f) of claim 16 until a desired amount of fluid is transmitted while maintaining the fluid directing means at the selected position.

18. A syringe apparatus for transmitting a fluid comprising:
(a) a first syringe having a generally hollow tube and a plunger for displacement within the hollow tube, the hollow tube having a fluid port for transmitting fluid relative to the hollow tube and the plunger having a piston in sealing engagement with the hollow tube and an actuator for effecting longitudinal displacement of the piston within the hollow tube to provide fluid transmission through the fluid port;

(b) a reservoir for holding the fluid;

(c) a hypodermic needle; and (d) a valve having an outside port connected with the hypodermic needle, for transmitting fluid, a reservoir port connected with the reservoir, and a syringe port connected with the fluid port of the hollow tube, the valve rigidly holding the hypodermic needle in fixed position relative to the first syringe and providing a first fluid flow path between the reservoir port and the syringe port and a second fluid flow path between the syringe port and the outside port, and the valve having a selector for alternatively selecting the first and second fluid flow paths.

19. The apparatus as recited in claim 18 comprising an elongated flexible connecting tube having a first end connected with the reservoir and having a second end connected with the reservoir port.

20. The apparatus as recited in claim 19 wherein the reservoir comprises a second syringe.

21. The apparatus as recited in claim 20 wherein at least one of the first and second syringes has index means to enable metering of a predetermined amount of fluid.

22. The apparatus as recited in claim 19 wherein the actuator comprises a finger loop and the second end of the hollow tube has two finger loops for one-handed operation of the first syringe.

* * * * *